(12) United States Patent
Corbier et al.

(10) Patent No.: US 7,005,417 B1
(45) Date of Patent: *Feb. 28, 2006

(54) ECHINOCANDIN DERIVATIVES, METHOD FOR PREPARING SAME AND USE AS ANTIFUNGAL AGENTS

(75) Inventors: Alain Corbier, Verrieres le Buisson (FR); Patrick Fauveau, Livry Gargan (FR); Nathalie Pietre-Dischamp, Ormesson sur Marne (FR); Laurent Schio, Bondy (FR); Pascale Vicat, Paris (FR)

(73) Assignee: Aventis Pharma S.A., (FR)

( * ) Notice: Subject to any disclaimer, the term of this patent is extended or adjusted under 35 U.S.C. 154(b) by 320 days.

This patent is subject to a terminal disclaimer.

(21) Appl. No.: 10/009,407

(22) PCT Filed: Jun. 8, 2000

(86) PCT No.: PCT/FR00/01569

§ 371 (c)(1),
(2), (4) Date: Jan. 25, 2002

(87) PCT Pub. No.: WO00/75178

PCT Pub. Date: Dec. 14, 2000

(30) Foreign Application Priority Data

Jun. 9, 1999 (FR) .................................. 99 07252

(51) Int. Cl.
*A61K 38/12* (2006.01)

(52) U.S. Cl. .......................... 514/11; 514/17; 530/317; 530/329

(58) Field of Classification Search ................ 530/317, 530/329; 514/11, 17
See application file for complete search history.

(56) References Cited

U.S. PATENT DOCUMENTS 6,677,429 B1 * 1/2004 Courtin et al. .............. 530/317

FOREIGN PATENT DOCUMENTS

| EP | 0644199 | 3/1995 |
|---|---|---|
| EP | 0736541 | 10/1996 |
| WO | 9613272 | 5/1996 |
| WO | 9823637 | 6/1998 |
| WO | 9929716 | 6/1999 |

OTHER PUBLICATIONS

Anderson et al., 2004, CAS:140:127185.*

Courtin et al., Jun. 17, 1999, WO 99/29716.*

* cited by examiner

*Primary Examiner*—Taofiq Solola
*Assistant Examiner*—Robert Shiao
(74) *Attorney, Agent, or Firm*—Charles A. Muserlian

(57) ABSTRACT

A subject of the invention is the compounds of formula (I):

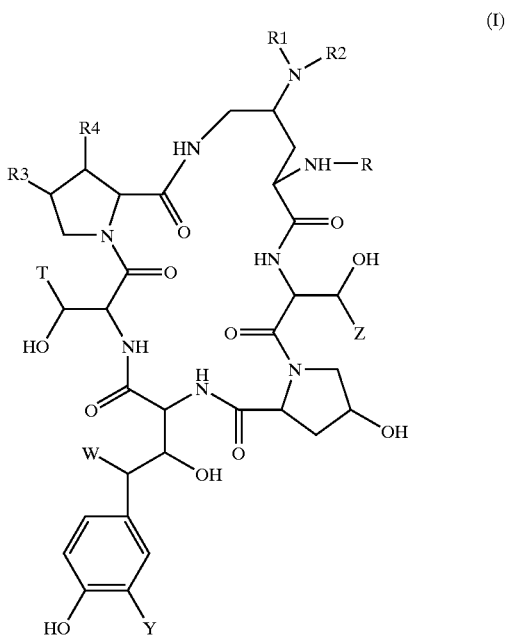

in which
either $R_1$ and $R_2$=H, OH, alkyl optionally substituted, or $NR_1$ form with the carbon carrying $NR_1R_2$ a double bond and $R_2$ is XRa, X being O, NH OR N-alkyl and Ra being H, alkyl optionally substituted,
or $R_2$ is e-N=C(—N-d)-N(f)-g
 $R_3$=H, OH, $CH_3$
 $R_4$=H, OH
 R=chain containing up to 30 carbon atoms, optionally containing one or more heteroatoms, one or more heterocycles,
 T=H, $CH_3$, $CH_2CONH_2$, $CH_2C\equiv N$, $(CH_2)_2NH_2$, $(CH_2)_2Nalk^+X^-$
 Y=H, OH, Halogen, $OSO_3H$
 W=H, OH
 Z=H or $CH_3$.

The products have of the antifungal properties.

20 Claims, No Drawings

US 7,005,417 B1

ECHINOCANDIN DERIVATIVES, METHOD FOR PREPARING SAME AND USE AS ANTIFUNGAL AGENTS

This application is a 371 of PCT/FR00/01569 filed Jun. 8, 2000.

The present invention relates to new derivatives of echinocandine, their preparation process and their use as antifungals.

A subject of the invention is in all the possible isomer forms as well as their mixtures, the compounds of formula (I):

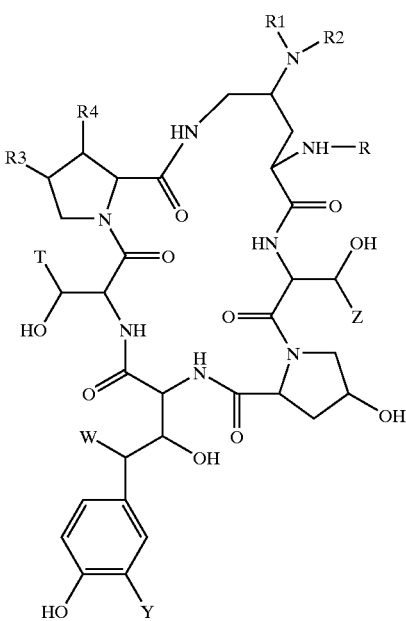

in which
either $R_1$ and $R_2$ identical to or different from one another, represent a hydrogen atom, a hydroxyl radical, a linear, branched or cyclic alkyl radical containing up to 8 carbon atoms optionally interrupted by an oxygen atom optionally substituted by a halogen atom, an OH radical, an

radical, a and b identical to or different from one another, representing a hydrogen atom or an alkyl radical containing up to 8 carbon atoms, a and b can optionally form with the nitrogen atom a heterocycle optionally containing one or more additional heteroatoms,
or $R_1$ forms with the endocyclic carbon atom carrying the

radical a double bond and or R2 represents an XRa radical, X representing an oxygen atom or an NH or N-alkyl radical-containing up to 8 carbon atoms and Ra represents a hydrogen atom, a linear, branched or cyclic alkyl radical containing up to 8 carbon atoms optionally substituted by one or more halogen atoms, by one or more OH, $CO_2H$, $CO_2$alk radicals, by an

radical, a' and b' representing a hydrogen atom, an alkyl radical containing up to 8 carbon atoms, a' and b' can form a heterocycle optionally containing one or more additional heteroatoms and/or by a heterocycle containing one or more heteroatoms or $R_2$ represents a

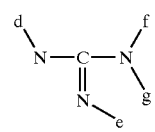

radical in which d, e, f and g represent a hydrogen atom or an alkyl radical containing up to 8 carbon atoms, f and g can moreover represent an acyl radical containing up to 8 carbon atoms, e and f can also form a ring optionally containing one or more heteroatoms,
$R_3$ represents a hydrogen atom, a methyl or hydroxyl radical
$R_4$ represents a hydrogen atom or a hydroxyl radical
R represents a radical chosen from the following radicals:

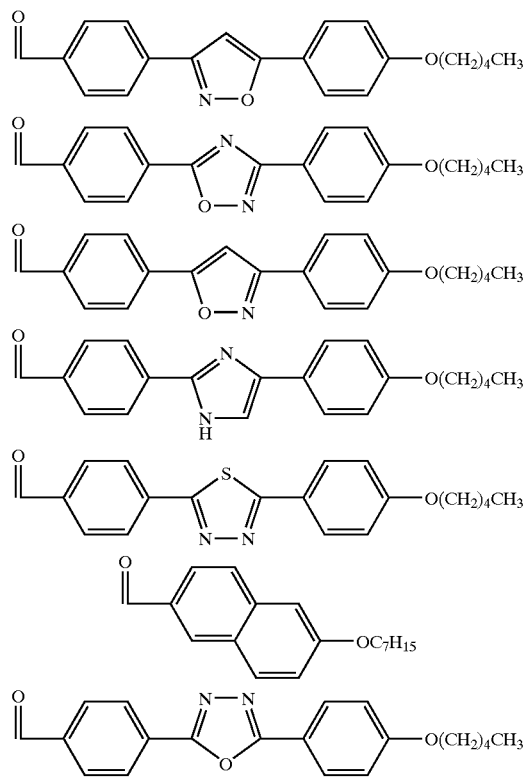

-continued

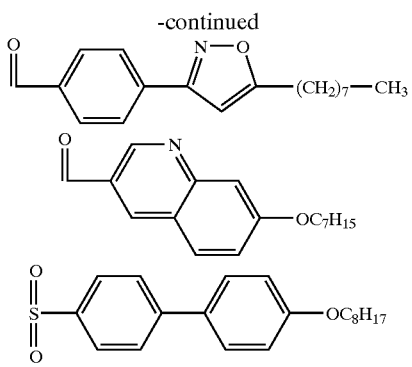

T represents a hydrogen atom, a methyl radical, a $CH_2CONH_2$, $CH_2C\equiv N$ radical, a $(CH_2)_2NH_2$ or $(CH_2)_2Nalk^+X^-$ radical, X being a halogen atom and alk an alkyl radical containing up to 8 carbon atoms, Y represents a hydrogen atom, a hydroxyl radical or a halogen atom or an $OSO_3H$ radical or one of the salts of this radical, W represents a hydrogen atom or an OH radical, Z represents a hydrogen atom or a methyl radical, as well as the addition salts with acids of the products of formula (I).

Among the addition salts with acids, there can be mentioned those formed with mineral acids, such as hydrochloric, hydrobromic, sulphuric or phosphoric acid or with organic acids such as formic, acetic, trifluoroacetic, propionic, benzoic, maleic, fumaric, succinic, tartaric, citric, oxalic, glyoxylic and aspartic acids, alkanesulphonic acids, such as methane or ethane sulphonic acid, arylsulphonic acids such as benzene or paratoluene sulphonic acids.

A more particular subject of the invention is the compounds of formula I in which T represents a hydrogen atom, those in which W represents a hydrogen atom, those in which Z-represents a methyl radical, those in which Y represents a hydrogen atom, those in which $R_3$ represents a methyl radical, those in which R4 represents a hydroxyl radical and those in which R represents a

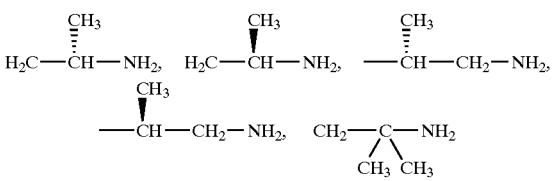

radical or a

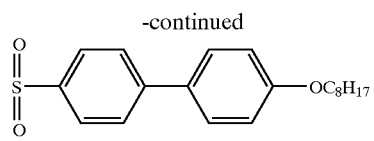

radical those in which $R_1$ represents a hydrogen atom, those in which $R_2$ represents a $(CH_2)_2NH_2$ radical those in which $R_2$ represents a

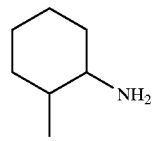

radical and in particular the

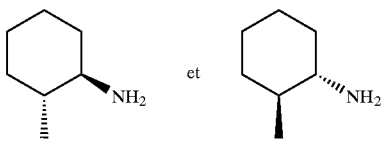

radicals as well as those in which R2 represents a $$H_2C-\overset{CH_3}{\underset{}{CH}}-NH_2, \quad H_2C-\overset{CH_3}{\underset{CH_3}{CH}}-NH_2, \quad -\overset{CH_3}{\underset{}{CH}}-CH_2-NH_2,$$

$$-\overset{CH_3}{\underset{}{CH}}-CH_2-NH_2, \quad CH_2-\overset{CH_3}{\underset{CH_3}{C}}-NH_2$$

radical.

A more particular subject of the invention is the compounds of formula I the preparation of which is given hereafter in the experimental part.

The compounds of formula (I) have useful antifungal properties; they are in particular active on *Candida albicans* and other *Candida* such as *Candida glabrata, krusei, tropicalis, pseudotropicalis, parapsilosis* and *Aspergillus fumigatus, Aspergillus flavus, Cryptococcus neoformans*.

The compounds of formula (I) can be used as medicaments in man or animals, in particular to combat invasive candidosis, digestive, urinary, vaginal or cutaneous candidosis, cryptococcosis, for example neuromeningeal, pulmonary or cutaneous cryptococcosis, bronchopulmonary and pulmonary aspergillosis and invasive aspergillosis in the immunosuppressed.

The compounds of the invention can also be used in the prevention of mycotic illnesses in the congenital or acquired immunosuppressed.

The compounds of the invention are not limited to a pharmaceutical use, they can also be used as fungicides in fields other than the pharmaceutical field.

Therefore a subject of the invention is, as antifungal compounds, the compounds of formula (I) as well as their addition salts with acids.

A subject of the invention is also the compounds of formula (I), as medicaments.

A most particular subject of the invention is the pharmaceutical compositions containing as active ingredient at least one compound of formula (I) or one of its addition salts with pharmaceutically acceptable acids.

These compositions can be administrered by oral, rectal, parenteral route or by local route as a topical application on the skin and mucous membranes, but the preferred routes are the oral and parenteral routes.

They can be solid or liquid and can be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated in the excipients usually used in these pharmaceutical compositions, such as talc, gum arabic, lactose, starch, magnesium stearate, cocoa butter, aqueous or non-aqueous vehicles, fatty matter of animal or vegetable origin, paraffin derivatives, glycols, various wetting, dispersing or emulsifying agents, preservatives.

A subject of the invention is also a preparation process for the compounds of formula (I) characterized in that a compound of formula (II)

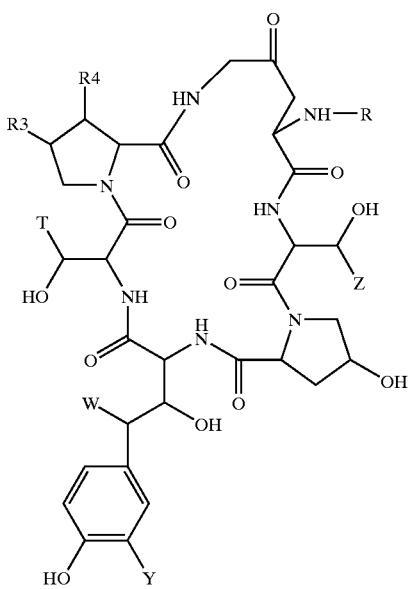

(II)

in which R, $R_3$, $R_4$, T, Y, W and Z retain their previous meaning, is subjected to the action of an amine or of an amine derivative capable of introducing the

radical
in which $R_1$ and $R_2$ retain their previous meaning and if desired to the action of a reducing agent,
and/or of a functionalization agent of the amine,
and/or of an acid in order to form the salt of the product obtained,
and/or of a separation agent of the different isomers obtained,
and in this way the compound of formula (I) as defined above is obtained.

The compounds of formula II used are new products and are in themselves a subject of the invention.

A subject of the invention is also a process characterized in that a compound of formula (III)

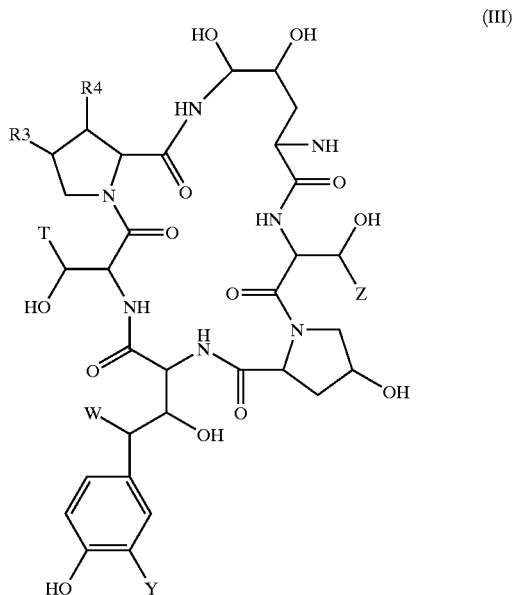

(III)

in which the different substituents retain their previous meaning is subjected to the action of an agent capable of replacing $NH_2$ by NHR, R retaining its previous meaning in order to obtain the compound of formula (IV)

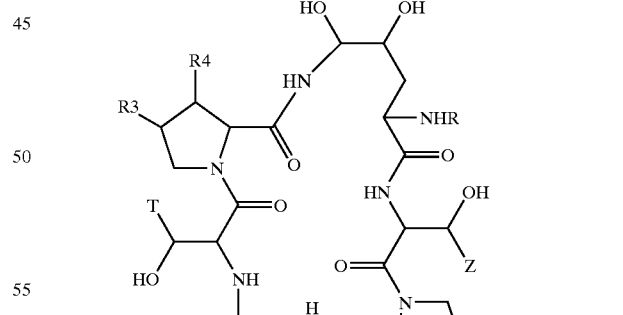

(IV)

which is subjected to the action of trimethylsilyl iodide in order to obtain the corresponding compound of formula (II)

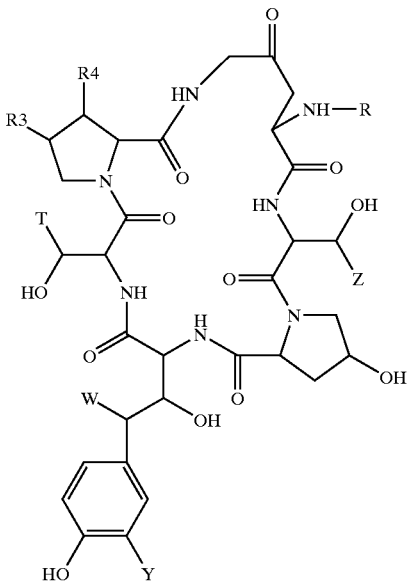

The compounds of formula III and IV used are new products and are in themselves a subject of the present invention.

Among the preferred products of formula III and IV, there can be quite particularly mentioned the products the preparation of which is given hereafter in the experimental part.

The following examples illustrate the invention without however limiting it:

Preparation 1: "Nucleus" of Deoxymulundocandine 2 g of deoxymulundocandine is dissolved in 20 ml of DMSO. This solution is poured into a suspension containing 120 g of Actinoplanes utahensis FH2264 in 870 ml of a KH2PO4, K2HPO4 buffer (pH: 6.8). The reaction mixture is maintained under agitation for 70 hours at 30° C. Filtration is carried out. The mycelium is washed with the phosphate buffer (pH: 6.8). The washing liquids and the filtrate are combined. The product obtained is chromatographed on a DIAION HP 20 resin and a product is obtained which is used as it is hereafter.

EXAMPLE 1

1-[4-[(2-aminoethyl)amino]-N2-[[4-[5-[4-pentyloxy)-phenyl]-3-isoxazolyl]-phenyl]-carbonyl]-L-ornithine]-4-(4-hydroxyphenyl)-L-threonine]-5-L-serine-echinocandine B (isomer A and isomer B)

STAGE A: 1-[(4R,5R)-4,5-dihydroxy-N2-[[4-[5-[4-(pentyloxy)-phenyl]-isoxazol-3-yl]-phenyl]-carbonyl]-L-ornithine]-4-[4-(4-hydroxyphenyl)-L-threonine]-5-L-serine-echinocandine B 16.8 g of the product of Preparation 1 is introduced under agitation and a nitrogen atmosphere into 552 ml of DMF. The reaction medium is agitated for 5 minutes and 19 g of the ester of formula

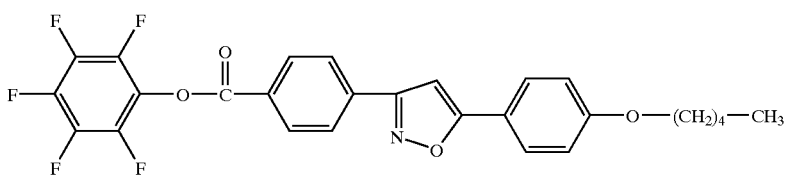

is added.

Agitation is carried out for 29 hours, followed by filtering and concentrating under reduced pressure. The residue is taken up in ether, followed by triturating, separating, washing with ethyl ether and chromatography on silica eluting with a methylene chloride methanol mixture (85/15). In this way the expected product is obtained rf=0.24

STAGE B: 1-[4-oxo-N2-[[4-[5-[4-(pentyloxy)-phenyl]-isoxazol-3-yl]-phenyl]-carbonyl]-L-ornithine]-4-[4-(4-hydroxyphenyl)-L-threonine]-5-L-serine-echinocandine B 6.12 ml of trimethylsilyl iodide is added to a suspension containing 16.1 g of the product of Stage A and 374 ml of acetonitrile is added. Then the reaction medium is heated for 15 minutes at 60° C. followed by hydrolyzing with a saturated solution of sodium thiosulphate. After bringing to dryness under reduced pressure chromatography is carried out on silica eluting with a methylene chloride, methanol, water mixture 86-13-1. The sought product is obtained rf=0.23.

Mass Spectrum
MH+=1083.6
Mna+=1105.6

STAGE C: 1-[4-[(2-aminoethyl)-amino]-N2-[[4-[5-[4-(pentyloxy)-phenyl]-3-isoxazol-yl]-phenyl]-carbonyl]-L-ornithine]-4-[4-(4-hydroxyphenyl)-L-threonine]-5-L-serine-echinocandine B trifluoroacetate (Isomer A and isomer B).

8.6 mg of NaBH$_3$CN is introduced into a mixture of 120 mg of the product of the preceding stage, 2.4 ml of methanol, 60 mg of ethylenediamine diacetate in the presence of activated 4A siliporite. The reaction mixture is maintained under agitation and under a nitrogen atmosphere for 18 hours, followed by filtering and concentrating. The product obtained is purified by semi preparative HPLC eluting with an acetonitrile /H$_2$O/TFA mixture (40-60-0.02%). 14.5 mg of sought product is recovered.
Mass spectrum
1127+=MH+
1149+=Mna+
The following are recovered:
Isomer A: 14.5 mg
Isomer B: 17.5 mg

EXAMPLE 2 trans-1-[4-[(2-aminocyclo-hexyl)-amino]-N2-[[4-[5-[4-(pentyloxy)-phenyl]-3-isoxazolyl]-phenyl]-carbonyl]-L-ornithine]-4-[4-(4-hydroxyphenyl)-L-threonine]-5-L-serine-echinocandine B trifluoroacetate (Isomer A and Isomer B)

Approximately 40 μl of acetic acid is added under agitation and under a nitrogen atmosphere to a solution containing 100 mg of the product obtained in Stage B of the preceding example 3 ml of methanol, 32 mg of (1R, 2R) (-)-1,2-diaminocyclohexane until a pH close to 6 is obtained, in the presence of activated 3A siliporite. Agitation is carried out for 5 minutes and 12 mg of NaBH$_3$CN is introduced. The reaction mixture is maintained under agitation for 18 hours. followed by filtering and concentrating under reduced pressure. The product obtained is purified by semi-preparative HPLC (eluent CH$_3$CN,H$_2$O,TFA 50-50-0.02%)
Isomer A wt=11 mg
Isomer B wt=14 mg
Mass spectrum
1181.5 MH+

EXAMPLE 3 trans-1-[4-[(2-aminocyclo-hexyl)-amino]-N2-[[4-[5-[4-(pentyloxy)-phenyl]-3-isoxazolyl]-phenyl]-carbonyl]-L-ornithine]-4-[4-(4-hydroxyphenyl)-L-threonine]-5-L-serine-echinocandine B trifluoroacetate (Isomer A and isomer B)

Operating as in Example 2 with (1S, 2S)-(-)-1,2-diaminocyclohexane, the following are obtained:
Isomer A=7.4 mg
Isomer B=10.8 mg
Mass spectrum
1181.5=MH+

EXAMPLE 4

1-[4-[(2(S)-aminopropyl)-amino]-N2-[[4-[5-[4-(pentyloxy)-phenyl]-3-isoxazolyl]-phenyl]-carbonyl]-L-ornithine]-4-[4-(4-hydroxyphenyl)-L-threonine]-5-L-serine-echinocandine B trifluoroacetate (Isomer A and isomer B)

By operating as in Example 1 the following are obtained:
Isomer A: 13 mg
Isomer B: 10 mg

EXAMPLE 5 trans-1-[4-[(2-aminocyclo-hexyl)-amino]-N2-[[4-[3-[4-(pentyloxy)-phenyl]-1,2,4-oxadiazol-5-yl]-phenyl]-carbonyl]-L-ornithine]-4-[4-(4-hydroxyphenyl)-L-threonine]-5-L-serine-echinocandine B trifluoroacetate STAGE A: 1-[(4R,5R)-4,5-dihydroxyN2-[[4-[3-[4-(pentyloxy)-phenyl]-1,2,4-oxadiazol-5-yl]-phenyl]-carbonyl]-L-ornithine]-4-[4-(4-hydroxyphenyl)-L-threonine]-5-L-serine-echinocandine B By operating as in Example 1 Stage A, the sought product is obtained.
Mass spectrum
1124=MNa+

STAGE B: 1-[4-oxo-N2-[[4-[3-[4-(pentyloxy)-phenyl]-1,2,4-oxadiazol-5-yl]-phenyl]-carbonyl]-L-ornithine]-4-[4-(4-hydroxyphenyl)-L-threonine]-5-L-serine-echinocandine B By operating as in Example 1 Stage B, the sought product is obtained.
Mass spectrum
1106.6=MNa+
1090.8=MH+

STAGE C: trans-1-[4-[(2-aminocyclo-hexyl)-amino]-N2-[[4-[3-[4-(pentyloxy)-phenyl]-1,2,4-oxadiazol-5-yl]-phenyl]-carbonyl]-L-ornithine]-4-[4-(4-hydroxyphenyl)-L-threonine]-5-L-serine-echinocandine B trifluoroacetate By operating as in Example 1 Stage C, starting from 150 mg of the product of Stage B, and 51.4 mg of (1S,2S)1,2-diaminocyclohexane, 165 mg of crude product is obtained which is purified by semi preparative HPLC (KROMASIL C18 column) (eluent: CH$_3$CN—H$_2$O-TFA 45-55-0.1).
The following are obtained:
Isomer A 10.8 mg
Isomer B 5.2 mg
Mass spectrum:
1204=MNa$^+$
1182=MHa$^+$

EXAMPLE 6

1-[4-[(2-aminoethyl)amino]-N2-[[4-[5-[4-(pentyloxy)-phenyl]-1,3,4-thiadiazol-2-yl]-phenyl]-carbonyl]-L-ornithine]-4-[4-(4-hydroxyphenyl)-L-threonine]-5-L-serine-echinocandine B trifluoroacetate STAGE A: 1-[(4R,5R)-4,5-dihydroxy-N2-[[4-[3-[4-(pentyloxy)-phenyl]-1,3,4-thiadiazol-2-yl]-phenyl]-carbonyl]-L-ornithine]-4-[4-(4-hydroxyphenyl)-L-threonine]-5-L-serine-echinocandine B A suspension containing 2 g of 4-[5-[4-(pentyloxy)-phenyl]-1,3,4-thiadiazol-2-yl]-benzoic acid, 30 ml of DMF and 30 ml of dioxan is agitated for 5 minutes at 20° C. and 1.55 ml of tributylamine and 7.74 ml of isobutyl chloroformate are added at O/±5° C. The reaction medium is agitated for 3 minutes at 0±5° C. then for 3 hours at ambient temperature. 4.53 g of the deoxymulundocandine nucleus obtained as in Preparation 1 is introduced. Agitation is carried out for 16 hours at 20° C., followed by concentrating to dryness. The residue is taken up in ethyl ether, followed by separating and washing with ethyl ether. After drying 7.8 g of product is obtained which is purified by chromatography on silica eluting with a methylene chloride-methanol-water mixture 86-13-1. 2.51 g of sought product is obtained.

STAGE B: 1-[4-oxo-N2-[[4-[5-[4-(pentyloxy)-phenyl]-1,2,4-thiadiazol-2-yl]-phenyl]-carbonyl]-L-ornithine]-4-[4-(4-hydroxyphenyl)-L-threonine]-5-L-serine-echinocandine B By operating as in Stage B of Example 1, the sought product is obtained.

STAGE C: 1-[4-[(2-aminoethyl)amino]-N2-[[4-[3-[4-(pentyloxy)-phenyl]-1,3,4-thiadiazolol-2-yl]-phenyl]-carbonyl]-L-ornithine]-4-[4-(4-hydroxyphenyl)-L-threonine]-5-L-serine-echinocandine B By operating as in Example 1, Stage C starting from the product of the preceding stage and ethylenediamine diacetate, the sought product is obtained.
Isomer A wt=8 mg
Isomer B wt=9 mg

EXAMPLE 7 trans 1-[4-[(2-aminocyclo-hexyl)-amino]-N2-[[4-[5-[4-(pentyloxy)-phenyl]-1,3,4-thiadiazol-2-yl]-phenyl]-carbonyl]-L-ornithine]-4-[4-(4-hydroxyphenyl)-L-threonine]-5-L-serine-echinocandine B trifluoroacetate By operating as in Example 1, starting from the product of Stage B of Example 5 (50 mg) and (1S,2S)(+)1,2-diaminocyclohexane (15.6 mg), the sought product is obtained.
Isomer A=4 mg
Isomer B=6.5 mg

EXAMPLE 8 trans 1-[4-[(2-aminocyclo-hexyl)-amino]-N2-[[4-[5-[4-(pentyloxy)-phenyl]-1,2,4-thiadiazol-2-yl]-phenyl]-carbonyl]-L-ornithine]-4-[4-(4-hydroxyphenyl)-L-threonine]-5-L-serine-echinocandine B trifluoroacetate (Isomer A and Isomer B)

By operating as in Example 1 Stage C starting from the product of Stage B of Example 5 (50 mg) and (1R,2R)-1,2-diaminocyclohexane (15.6 mg), the sought product is obtained.
Isomer A=8.8 mg
Isomer B=10.6 mg Example: Pharmaceutical Composition:
Tablets were prepared containing:
Product of Example 1 . . . 150 mg
Excipient s.q.f. . . . 1 g
(Detail of excipient: starch, talc, magnesium stearate).

Pharmacological Study

A—Inhibition of the Glucan Synthase of *Candida albicans*
*Candida albicans* membranes were purified according to the process described by Tang et al Antimicrob. Agents Chemother 35, 99–103, 1991. 22.5 µg of membrane proteins are incubated in a mixture of 2 Mm of 14C-UDP glucose (specific activity=0.34 mCi./mmol, 50 µg of α-amylase, 1 Mm of dithiotreitol (DTT), 1 Mm EDTA, 100 Mm NaF, 7 µM of GTP-γ-S, 1 M of sucrose and 50 Mm of Tris-HCL (pH 7.8) in a volume of 100 µl. The medium is incubated at 25° C. for 1 hour and the reaction is terminated by adding TCA at a final concentration of 5%. The reaction mixture is transferred onto a pre-humidified glass fibre filter. The filter is washed, dried and its radioactivity is counted.

Mulundocandine is used as a positive control.
Control of the vehicle is carried out with the same quantity of 1% DMSO. The results obtained show that in this test the products of the invention show a good activity in particular the products of Example 1.

B—Activity on the *Aspergillus fumigatus* Enzyme
The enzyme is prepared according to the process of Beaulieu et al.(Antimicrob. Agents Chenother 38, 937–944, 1994.

The protocol used is identical to the protocol described above for the enzyme of *Candida albicans* except that dithiotreitol is not used in the reaction mixture.

In this test the products show a good activity.

What is claimed is:
1. A compound selected from the group consisting of all possible steroisomeric forms and their mixtures of a compound of the formula

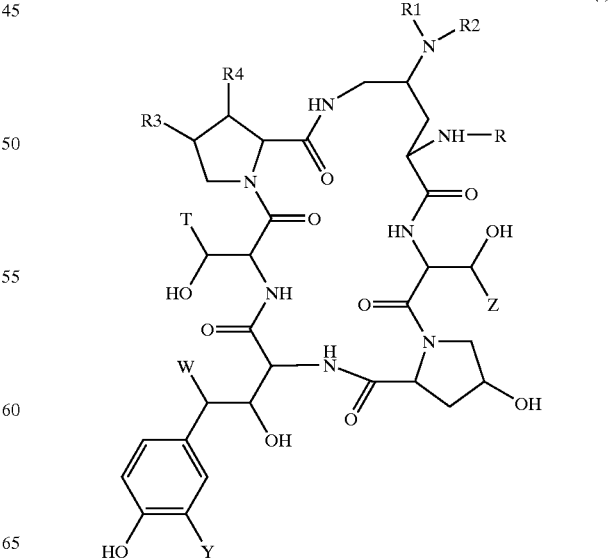

(I)

wherein either $R_1$ and $R_2$ are individually selected from the group consisting of hydrogen, hydroxyl, alkyl and cycloalkyl of up to 8 carbon atoms optionally interrupted by oxygen and optionally substituted by a member selected from the group consisting of

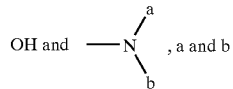

are individually hydrogen or alkyl of 1 to 8 carbon atoms or $R_1$ forms with the endocyclic carbon atom carrying

a double bond and R2 is —XRa, X is selected from the group consisting of oxygen, —NH— or —N-alkyl of 1 to 8 carbon atoms and Ra is selected from the group consisting of hydrogen, alkyl or cycloalkyl of up to 8 carbon atoms substituted by at least one member of the group consisting of halogen, —OH, —$CO_2H$, —$CO_2$alk,

a' and b' are hydrogen or alkyl of 1 to 8 carbon atoms or $R_2$ is

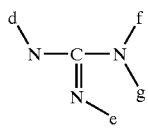

in which d, e, f and g are hydrogen or alkyl of 1 to 8 carbon atoms, f and g can also be acyl of up-to 8 carbon atoms, $R_3$ is selected from the group consisting of hydrogen, methyl and hydroxyl, $R_4$ is hydrogen or hydroxyl, R is selected from the group consisting of

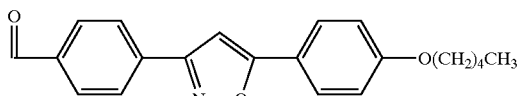
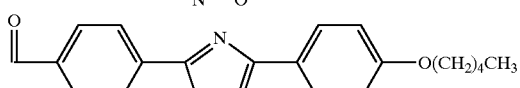
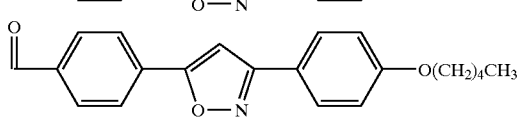

-continued

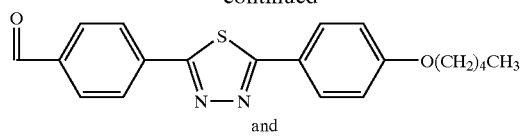
and
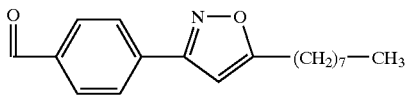

T is selected from the group consisting of hydrogen, methyl, —$CH_2CONH_2$, —$CH_2CN$, —$(CH_2)_2NH_2$ and —$(CH_2)Nalk^+X^-$, X is halogen and alk is alkyl of up to 8 carbon atoms, Y is selected from the group consisting of hydrogen, hydroxyl, halogen and $OSO_3H$ and a salt thereof, W is hydrogen or —OH, Z is hydrogen or methyl and a non-toxic, pharmaceutically acceptable acid addition salt thereof.

2. A compound of claim 1 in which T is hydrogen.

3. A compound of claim 1 in which W is hydrogen.

4. A compound of claim 1 in which Z is methyl.

5. A compound of claim 1 in which Y is hydrogen.

6. A compound of claim 1 in which $R_3$ is methyl.

7. A compound of claim 1 in which $R_4$ is hydroxyl.

8. A compound of claim 1 in which R is selected from the group consisting of

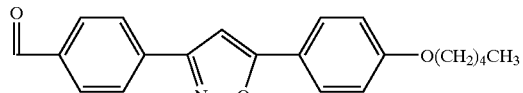
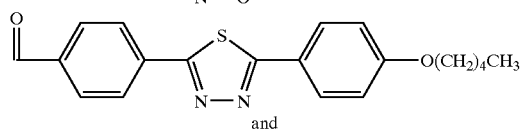
and
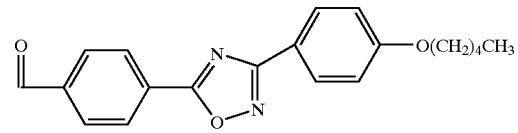

9. A compound of claim 1 in which $R_1$ is hydrogen.

10. A compound of claim 1 in which $R_2$ is $(CH_2)_2NH_2$.

11. A compound of claim 1 in which $R_2$ is

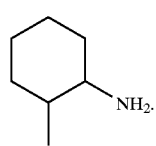

12. A compound of claim 1 in which $R_2$ is selected from the group consisting of

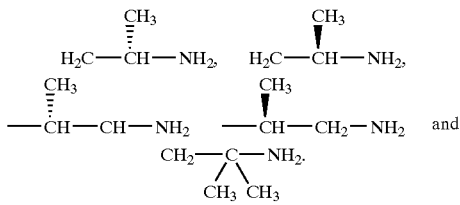

and

13. A compound of claim 1 selected from the group consisting of

1-[4-[(2-aminoethyl)-amino]-N2-[[4-[5-[4-(pentyloxy)-phenyl]-3-isoxazolyl]-3-phenyl]-carbonyl]-L-ornithine]-4-[4-(4-hydroxyphenyl)-L-threonine]-5-L-serine-echinocandine B trifluoroacetate, trans-1-[4-[(2-aminocyclohexyl)-amino]-N2-[[4-[5-[4-(pentyloxy)-phenyl]-3-isoxazolyl]-phenyl]-carbonyl]-L-ornithine]-4-[4-(4-hydroxyphenyl)-L-threonine]-5-L-serine-echinocandine B trifluoroacetate, 1-[4-[(2(S)-aminopropyl)-amino]-N2-[[4-[5-[4-(pentyloxy)-phenyl]-3-isoxazolyl]-phenyl]-carbonyl]-L-ornithine]-4-[4-(4-hydroxyphenyl)-L-threonine]-5-L-serine-echinocandine B trifluoroacetate, 1-[4-[(2-aminoethyl)amino]-N2-[[4-[5-([4-(pentyloxy)-phenyl]-1,3,4-thiadiazol-2-yl]-phenyl]-carbonyl]-L-ornithine]-4-[4-(4-hydroxyphenyl)-L-threonine]-5-L-serine-echinocandine B trifluoroacetate, trans 1-[4-[(2-aminocyclohexyl)-amino]-N2-[[4-[5-[4-(pentyloxy)-phenyl]-1,3,4-thiadiazol-2-yl]-phenyl]-carbonyl]-L-ornithine]-4-[4-(4-hydroxyphenyl)-L-threonine]-5-L-serine-echinocandine B trifluoroacetate and trans 1-[4-[(2-aminocyclohexyl)-amino]-N2-[[4-[3-[4-(pentyloxy)-phenyl]-1,2,4-oxadiazol-5-yl]-phenyl-]-carbonyl]-L-ornithine]-4-[4-(4-hydroxyphenyl)-L-threonine]-5-L-serine-echinocandine B trifluoroacetate.

14. A process for the preparation of a compound of claim 1 reacting a compound of the formula

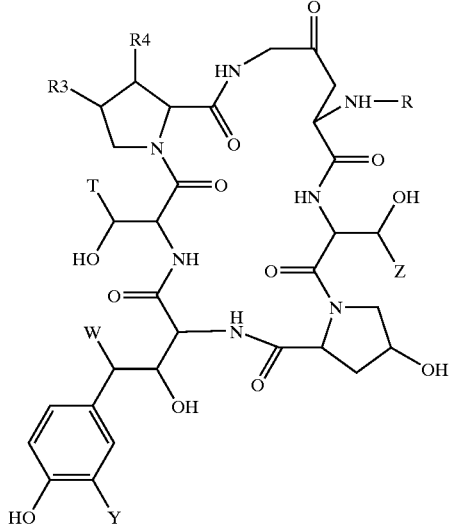

(II)

in which R, $R_3$, $R_4$, T, Y, W and Z are defined as in claim 1 with an amine or of an amine derivative capable of introducing

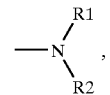

in which R1 and R2 are defined as in claim 1
and optionally then with a reducing agent,
and/or a functionalization agent of the amine,
and/or an acid to form the salt of the product of claim 1,
and/or a separation agent of the different isomers obtained.

15. A compound of the formula

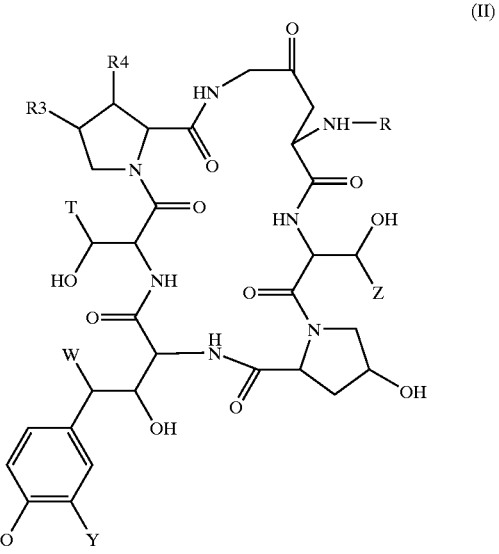

(II)

wherein R, $R_3$, $R_4$, T, Y, W and Z are defined as in claim 1.

16. A process of claim 14 wherein a compound of the formula

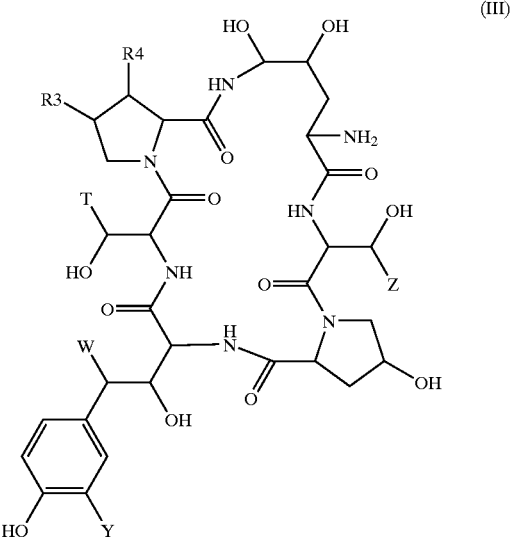

(III)

$R_3$, $R_4$, T, W, Y and Z are defined as in claim 14 reacted with an agent capable of replacing —$NH_2$ by —NHR, R being defined as in claim 14 to obtain a compound of the formula

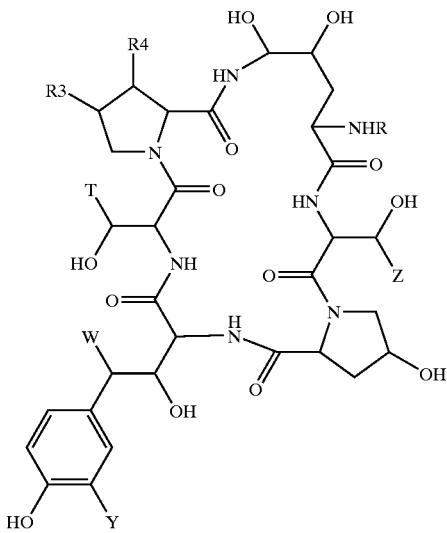

(IV)

reacting the said compound with trimethylsilyl iodide to obtain the corresponding compound of the formula

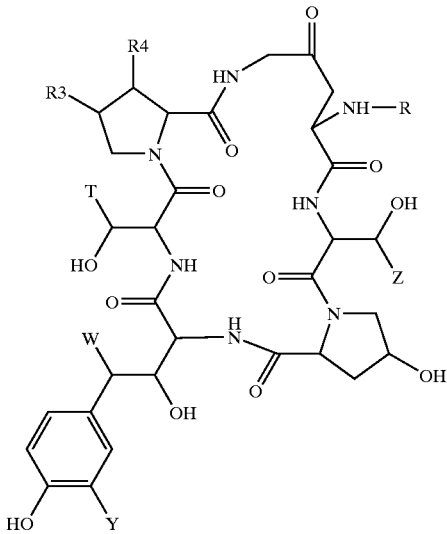

(II)

17. A compound of claim 11 wherein $R_2$ is

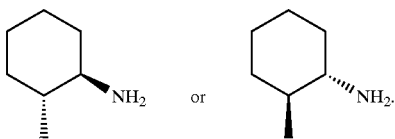

18. A compound of the formula

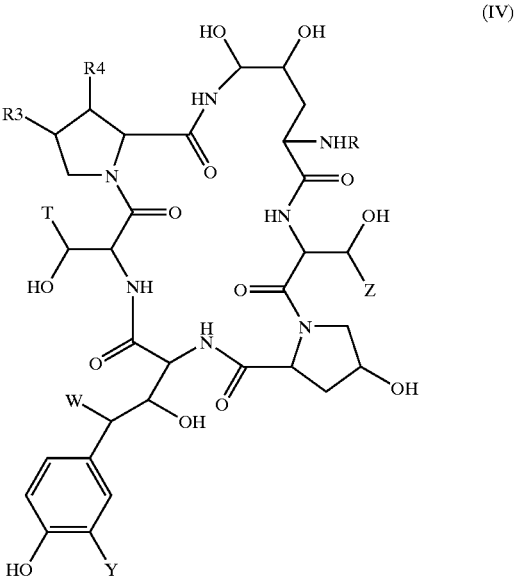

(IV)

wherein R, $R_3$, $R_4$, T, W, Y and Z are defined as in claim 1.

19. An antifungal composition comprising an antifungally effective amount of a compound of claim 1 and an inert pharmaceutical carrier.

20. A method of treating fungal infections in warm-blooded animals comprising administering to warm-blooded animals in need thereof an antifungally effective amount of a compound of claim 1.

* * * * *